United States Patent
Perera et al.

(10) Patent No.: US 11,779,874 B2
(45) Date of Patent: Oct. 10, 2023

(54) AIR FILTERS

(71) Applicant: UNIVERSITY OF BATH, Bath (GB)

(72) Inventors: Semali Priyanthi Perera, Bath (GB); Barry David Crittenden, Bath (GB); Olivier Camus, Bath (GB); Yong-Min Chew, Bath (GB); Ramya G, Bath (GB)

(73) Assignee: University of Bath, Bath (GB)

( * ) Notice: Subject to any disclaimer, the term of this patent is extended or adjusted under 35 U.S.C. 154(b) by 713 days.

(21) Appl. No.: 16/605,997

(22) PCT Filed: Apr. 18, 2018

(86) PCT No.: PCT/GB2018/051018
§ 371 (c)(1),
(2) Date: Oct. 17, 2019

(87) PCT Pub. No.: WO2018/193249
PCT Pub. Date: Oct. 25, 2018

(65) Prior Publication Data
US 2020/0338493 A1 Oct. 29, 2020

(30) Foreign Application Priority Data
Apr. 18, 2017 (GB) .................................. 1706126

(51) Int. Cl.
*B01D 53/02* (2006.01)
*B01D 53/04* (2006.01)
(Continued)

(52) U.S. Cl.
CPC .............. *B01D 53/04* (2013.01); *B01J 20/18* (2013.01); *B01J 20/20* (2013.01); *B01J 20/226* (2013.01); *B01J 20/28045* (2013.01);
*B01D 2253/102* (2013.01); *B01D 2253/108* (2013.01); *B01D 2253/1122* (2013.01);
(Continued)

(58) Field of Classification Search
CPC .............. B01D 53/04; B01D 2253/102; B01D 2253/108; B01D 2253/1122; B01D 2253/204; B01D 2257/91; B01D 2258/06; B01J 20/18; B01J 20/20; B01J 20/226; B01J 20/28045; C08J 9/12; C08J 9/35
See application file for complete search history.

(56) References Cited

U.S. PATENT DOCUMENTS 3,813,347 A  5/1974  Hayes
3,865,758 A  2/1975  Yoshida et al.
(Continued)

FOREIGN PATENT DOCUMENTS

CN  1134949 A  11/1996
CN  101757902 A  6/2010
(Continued)

OTHER PUBLICATIONS

International Search Report and Written Opinion of the ISA for PCT/GB2018/051018, mailed.
(Continued)

*Primary Examiner* — Christopher P Jones
(74) *Attorney, Agent, or Firm* — Nixon & Vanderhye P.C.

(57) ABSTRACT

The present invention provides an air filter comprising a polymer foam and an adsorbent material wherein said polymer foam comprises metal particles.

23 Claims, 9 Drawing Sheets

(51) Int. Cl.
  *B01J 20/18*  (2006.01)
  *B01J 20/20*  (2006.01)
  *B01J 20/22*  (2006.01)
  *B01J 20/28*  (2006.01)
  *C08J 9/12*  (2006.01)
  *C08J 9/35*  (2006.01)

(52) U.S. Cl.
  CPC .... *B01D 2253/204* (2013.01); *B01D 2257/91* (2013.01); *B01D 2258/06* (2013.01); *C08J 9/12* (2013.01); *C08J 9/35* (2013.01)

(56) References Cited

U.S. PATENT DOCUMENTS

| | | | |
|---|---|---|---|
| 5,000,813 | A | 3/1991 | Hill |
| 5,135,959 | A | 8/1992 | Hill |
| 5,877,226 | A | 3/1999 | Tsuda et al. |
| 8,191,435 | B2 | 6/2012 | Grate et al. |
| 9,042,946 | B2 | 5/2015 | Suzuki et al. |
| 2005/0005771 | A1* | 1/2005 | Lomax ............ B01D 53/047 96/121 |
| 2006/0182944 | A1 | 8/2006 | Leavitt |
| 2007/0281854 | A1* | 12/2007 | Harbour ............ B01J 23/755 502/200 |
| 2008/0178738 | A1 | 7/2008 | Chan et al. |
| 2009/0136809 | A1* | 5/2009 | Wang ............ B82Y 30/00 429/129 |
| 2010/0181212 | A1* | 7/2010 | Koch ............ B01J 20/28042 502/402 |
| 2011/0034579 | A1 | 2/2011 | Pinto et al. |
| 2011/0196054 | A1* | 8/2011 | Delaviz ............ C08J 9/146 521/139 |
| 2013/0036908 | A1 | 2/2013 | Jones et al. |
| 2013/0175026 | A1 | 7/2013 | Chakraborty et al. |
| 2014/0039082 | A1 | 2/2014 | Peterson et al. |
| 2015/0069292 | A1* | 3/2015 | Inoue ............ B01J 20/267 525/328.2 |
| 2016/0068646 | A1 | 3/2016 | Kumaki et al. |
| 2016/0311139 | A1 | 10/2016 | Tamagnini |
| 2017/0296967 | A1* | 10/2017 | Escalettes ............ B01J 20/3217 |

FOREIGN PATENT DOCUMENTS

| | | |
|---|---|---|
| CN | 103958052 A | 7/2014 |
| CN | 105254887 A | 1/2016 |
| EP | 0 368 612 A1 | 5/1990 |
| EP | 1 076 074 | 2/2001 |
| EP | 2 841 182 | 3/2015 |
| GB | 1335 133 A | 10/1973 |
| JP | 49-131988 A | 12/1974 |
| JP | 59219341 A | 12/1984 |
| JP | 10-114812 A | 5/1998 |
| JP | 2002-238981 A | 8/2002 |
| JP | 2002-317620 A | 10/2002 |
| JP | 2004-041445 A | 2/2004 |
| JP | 3116927 U | 11/2005 |
| JP | 2013-155342 A | 8/2013 |
| JP | 53-15461 B2 | 10/2013 |
| JP | 2014-46258 A | 3/2014 |
| PL | 230174 B1 | 9/2018 |
| WO | 2004/007583 A1 | 1/2004 |
| WO | 2007/028176 A1 | 3/2007 |
| WO | 2007/149418 | 12/2007 |
| WO | 2010/108328 | 9/2010 |
| WO | 2013/008019 | 1/2013 |
| WO | 2013/159797 | 10/2013 |
| WO | 2016/135237 A2 | 9/2016 |
| WO | 2016/135257 A2 | 9/2016 |

OTHER PUBLICATIONS

International Preliminary Report on Patentability forPCT/GB2018/051018, dated Aug. 7, 2019, 22 pages.
Written Opinion of the International Preliminaiy Examining Authority dated Apr. 4, 2019, 8 pages.
Search Report dated Aug. 27, 2021 issued in Chinese Application No. 201880035700.0 with English translation (6 pages).
Office Action dated Sep. 2, 2021 issued in Chinese Application No. 201880035700.0 with English translation (19 pages).
Office Action dated Jun. 13, 2022 issued in European Application No. 18721108.1 (11 pages).
Examination Report dated May 20, 2022 issued in GB Application No. 1706126.8 (6 pages).
Examination Report dated Dec. 10, 2021 issued in GB Application No. 1706126.8 (2 pages).
Office Action dated Apr. 6, 2022 issued in Chinese Application No. 201880035700.0 with English translation (21 pages).
Search Report dated Sep. 21, 2017 issued in GB Application No. 1706126.8 (6 pages).
First Search Report dated Apr. 30, 2018 issued in GB Application No. 1706126.8 (3 pages).
Second Search Report dated Apr. 30, 2018 issued in GB Application No. 1706126.8 (3 pages).
Third Search Report dated Apr. 30, 2018 issued in GB Application No. 1706126.8 (3 pages).
Office Action dated Feb. 2, 2022 issued in Japanese Application No. 2019-557451 with English language translation (6 pages).
Decision of Rejection dated Oct. 10, 2022 issued in related Chinese Application No. 201880035700.0 with English translation (13 pages).
Examination Report dated Nov. 7, 2022 issued in related GB Application No. 1706126.8 (2 pages).

* cited by examiner

AIR FILTERS

This application is the U.S. national phase of International Application No. PCT/GB2018/051018 filed 18 Apr. 2018, which designated the U.S. and claims priority to GB Patent Application No. 1706126.8 filed 18 Apr. 2017, the entire contents of each of which are hereby incorporated by reference.

FIELD OF THE INVENTION

The present invention relates to air filters, methods of making and uses thereof. In particular, the present invention relates to air filters comprising an antimicrobial or antibacterial material and a material for removing volatile organic compounds by adsorption. The present invention also relates to polymer foams suitable for use in said air filters and which provide at least antibacterial and/or antiviral properties and methods of making said polymer foams. The present invention also relates to composite materials which possess antimicrobial or antibacterial and adsorptive properties for use in said air filter and methods of making said composites. The present invention also relates to the polymer foams and composite materials obtainable from said methods. The air filters in accordance with the present invention are useful in a range of environments and are particularly useful in the airline industry, including in aircraft cabins.

BACKGROUND OF THE INVENTION

Air filters are used in a broad range of environments. There are particularly stringent requirements placed on air filters which are used in various environments such as the health industry and the airline industry, for example in aircraft cabins. It is desirable for such a filter to be capable of removing volatile organic compounds (VOC), odours and trapping, and preferably killing, bacteria and/or virus and/or fungus. Providing an air filter that is able to provide all of these functions presents an on-going challenge and there is an on-going significant need to provide such a filter for use in a range of environments.

Currently in air filters suitable for use in aircraft cabins, generally air passes from the bottom of the cabin through recirculation filters into a mixing chamber where it is mixed with outside air. Typically, the air is mixed with outside air (about 50/50 by volume) and then passed back into the cabin. Standard airline cabin air exchange rates range from 15 to 20 air changes per hour. The ventilation capacity varies substantially, dependent on the aircraft type but typically averages 4.7 L/s (10 ft$^3$/min). Some filters are used on commercial aircraft where air is circulated every 3 to 5 minutes. Many filters which are currently in use simply trap the bacteria and do not kill them.

So called High Efficiency Particulate Arrestance, or Arresting (HEPA) filters are one of the types of air filters currently used in medical facilities, automobiles, aircraft and homes. To qualify as HEPA by US government standards an air filter must remove from air that passes through it, 99.97% of particles that have a size of 0.3 μm. However, there are a number of disadvantages associated with HEPA filters. HEPA filters cannot be cleaned to remove particulate, microbial agents and dust loading and must be replaced as a complete assembly often at significant cost. As the particle load increases so will the resistance to air flow and hence a pressure drop across the filter will occur. In some applications, uneven filter loading will cause non uniform airflow through the filter and decreased effectiveness.

Polymer foams are used in a wide variety of applications such as packaging and insulation. Polymer foams are made up of a solid and gas phase mixed together to form a foam. The resulting foam has a polymer matrix with air bubbles and/or air tunnels incorporated in it which may be referred to as a closed cell or an open cell structure. The gas that is used in the foam is termed a blowing agent and may be chemical or physical in nature. Physical blowing agents are gases that do not react chemically with the foaming process and are therefore inert to the polymer forming the matrix. Chemical blowing agents are chemicals that take part in a reaction or decompose giving off chemicals in the process.

SUMMARY OF THE INVENTION

In accordance with a first aspect of the present invention, there is provided an air filter comprising a polymer foam and an adsorbent material wherein said polymer foam comprises metal particles. The metal particles may be present as a metal and/or a metal compound and/or a metal alloy. The adsorbent material may be comprised in a polymer foam. This feature may be referred to herein as an adsorbent polymer foam or polymer adsorbent foam. The combination of the polymer foam comprising metal particles and adsorbent material may be referred to herein as an active part or active element. The adsorbent material is present in addition to the polymer foam which comprises metal particles. The metal particles possess antimicrobial, e.g. antibacterial properties.

The metal particles in the polymer foam may be present in an amount based on the total weight of the filled polymer foam of at least about 20 wt % or greater than about 30 wt % to about 80 wt %, for example about 40-80 wt %, for example about 50-80 wt % or about 60-80 wt %.

In the adsorbent polymer foam, the adsorbent material may be present based on the total weight of the adsorbent polymer foam of at least about 55 wt %, or at least about 60 wt % for example about 55 wt % or about 60 wt % to about 80 wt % or to about 90 wt % or to about 95 wt % or to about 100 wt %.

The air filter may further comprise a structure for housing the combination of adsorbent material and polymer foam and metal particles. The housing structure may typically comprise an air inlet and air outlet and may also comprise an air distributor such as an air distributor plate. The combination of polymer foam (including the metal particles) and an adsorbent material may be referred to herein as the active part or active element of the air filter. The active part of the air filter may be present in the form of a composite material or the polymer foam comprising metal particles and adsorbent material, e.g. adsorbent polymer foam, may be separate features which may or may not be in contact. The active element constitutes a further aspect of the present invention. There is also provided in a second aspect in accordance with the present invention an active element comprising (i) a polymer foam and (ii) an adsorbent material wherein the polymer foam comprises metal particles and wherein the polymer foam, adsorbent material and metal particles are in the form of a composite material suitable for use in the air filter in accordance with the first aspect of the present invention and wherein the metal particles are present in an amount greater than about 30 wt % or from about 50 wt % or about 60 wt % to about 80 wt % based on the total weight of the filled polymer foam, and wherein the metal particles are selected from one or any combination of copper, zinc, silver, potassium, selenium, titanium, gold, palladium, platinum, which are present as metals, metal compounds or metal alloys or any combination thereof.

In a third aspect of the present invention there is provided a polymer foam suitable for use in the air filter in accordance with the first aspect of the present invention wherein the polymer foam comprises metal particles, and wherein the metal particles are present in an amount of greater than about 30 wt % or from about 50 wt % or from about 60 wt % to about 80 wt % based on the total weight of the filled polymer foam. The metal particles may be selected from one or any combination of copper, zinc, silver, potassium, selenium, titanium, gold, palladium, platinum. The metal particles may be present as a metal and/or a metal compound and/or a metal alloy.

In a fourth aspect of the present invention there is provided a polymer foam suitable for use in the air filter in accordance with the first aspect of the present invention wherein the polymer foam comprises metal particles and the polymer comprises or consists of polyimide. The metal particles may be present in an amount of greater than about 30 wt % or from about 50 wt % or from about 60 wt % to about 80 wt % based on the total weight of the filled polymer foam.

In a fifth aspect there is provided a method of making a polymer foam in accordance with the third or fourth aspect of the present invention comprising combining a polymer composition or polymer forming composition and particles of metal and foaming the polymer composition or polymer forming composition using a gas to form a polymer foam wherein the metal particles are optionally selected from one or any combination of copper, zinc, silver, potassium, selenium, titanium, gold, palladium, platinum. The metal particles may be present as a metal and/or a metal compound and/or a metal alloy.

In a sixth aspect, there is provided a method of making: (A) a polymer foam comprising metal particles or; (B) a composite material comprising (c) a polymer foam and an adsorbent or (d) a polymer foam, metal particles and an adsorbent, said method comprising forming a mixture by:
 (i) dissolving a monomer, polymer precursor or polymer in a solvent to form a solution;
 (ii) combining the solution from (i) with water to form a blowing agent; and further combining therewith;
 (iii) an isocyanate;
 (iv) a catalyst;
 (v) a pore former;
 (vi) metal particles and/or an adsorbent;
 (vii) homogenising the mixture.

Typically, homogenisation may take place at about 20° C. or at least about 20° C., and/or at least or at about 5000 rpm or at about 10,000 rpm, for example about 5000 rpm to about 10,000 rpm. Homogenisation may take place for at least or equal to about 30 seconds.

Hence, the polymer foam formed in the sixth aspect may comprise metal particles, or may be an adsorbent polymer foam or a composite polymer foam comprising adsorbent and metal particles. The products obtainable from the fifth or sixth aspect of the present invention also constitute a further aspect in accordance with the present invention.

In a seventh aspect there is provided a method of making an air filter comprising combining a polymer foam comprising metal particles and adsorbent material with a structure for housing said polymer foam and adsorbent material, wherein the housing structure comprises an air inlet and air outlet and optionally an air distributor, for example an air distributor plate. The combination of polymer foam comprising metal particles and adsorbent material may be in the form of a composite or there may be provided a polymer adsorbent foam plus polymer foam comprising metal particles.

In a further aspect there is provided the use of an air filter in accordance with the first aspect of the present invention for filtering air and additionally a method of filtering air comprising passing air through the air filter of the first aspect of the present invention.

In a further aspect, there is provided the use of an active element in accordance with the present invention, for example in accordance with the second aspect, for filtering air and a method of filtering air comprising passing air through the active element in accordance with the present invention.

In filtering air, the levels of bacteria and/or VOCs are reduced when comparing the air as it enters the air filter or active element with the air as it exits or just after it has exited the air filter or active element.

In the various aspects of the invention, the metal may be present as a metal or a metal compound or a metal alloy or any combination of said metal, metal compound or metal alloy. The metal, metal alloy or metal compound typically possesses antimicrobial, e.g. antibacterial properties. The metal, metal alloy or metal compound is preferably selected from one of, or any combination of, copper, zinc, silver, potassium, selenium, titanium, gold, palladium, platinum, a compound of any one of copper, zinc, silver, potassium, selenium, titanium, gold, palladium, platinum, an alloy of any one of copper, silver, zinc, potassium, selenium, titanium, gold, palladium, platinum. For example, the particles of metal may comprise a combination of copper and zinc or may comprise a combination of a copper compound and a zinc compound or a combination of copper alloy and zinc alloy. In the various aspects of the invention, the polymer may be selected from polyimide, polyurethane, polymers of intrinsic microporosity (PIMs), polyvinylidene difluoride (PVDF), Polyethersulfone (PES), cellulose or bio-degradable polymers such as polylactic acid (PLA) and poly(lactic-co-glycolic acid) (PLGA) and poly(vinylpyrrolidinone).

Hereinafter, the present invention will tend to focus on the use of air filters in the airline industry, however the air filters described herein are also useful in a range of other environments where air filters are often used, including in hospitals and surgeries where clean air is essential for a healthy working environment and vehicles other than aircraft such as automobiles.

BRIEF DESCRIPTION OF THE DRAWINGS

This and other aspects of the present invention will now be described in more detail, with reference to the appended drawings showing embodiments of the invention.

DETAILED DESCRIPTION OF THE INVENTION

Figure 1A:
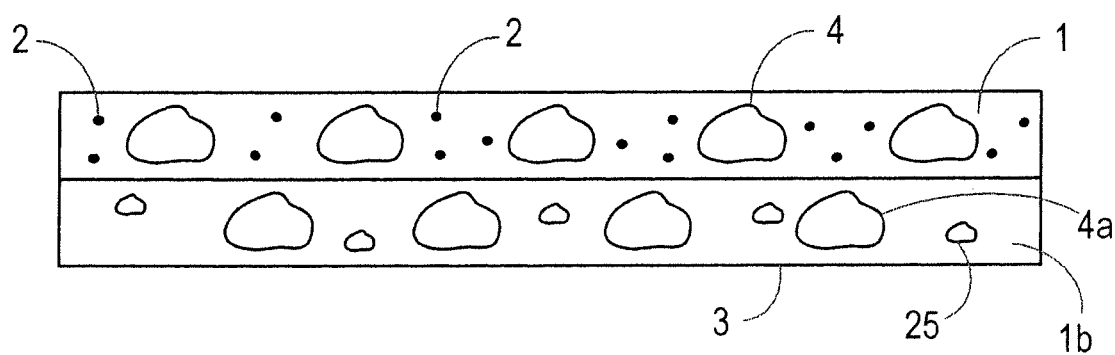
FIG. 1a shows a representation of the combination of polymer foam and adsorbent material suitable for use in an air filter in an embodiment of the invention.

The present invention will now be described more fully hereinafter with reference to the accompanying drawings, in which currently preferred embodiments of the invention are shown. This invention may, however, be embodied in many different forms and should not be construed as limited to the embodiments set farther herein; rather, these embodiments are provided for thoroughness and completeness, and fully convey the scope of the invention to the skilled person. Like reference numerals in the drawings refer to like elements throughout.

Air Filter

The air filter may comprise a first and a second layer, wherein the first layer comprises the polymer foam and a second layer in contact with or adjacent to said first layer, wherein the second layer is or comprises an adsorbent material. The first layer may be deposited on the second layer or the second layer may be deposited on the first layer. The first and second layers may be spaced and not in direct contact. These embodiments of the invention may be referred to herein as being in a sandwich or dual form. The layer or layers may be referred to as substrate or substrates as appropriate. The combination of polymer foam (and metal particles) and adsorbent material or adsorbent polymer foam may be referred to herein as the active part or active element of the air filter for ease of reference. The active element at least reduces the level of bacteria in air which passes through said active element and the associated air filter.

The precise design of the air filter may depend on a number of variables including desired removal efficiency of bacteria and/or volatile organic compounds, air flow velocity, installation configuration, acceptable pressure drop and life requirements. Important design considerations include one or more of minimum pressure drop, minimum weight, high collapse strength, energy savings, long service life. Preferably the air filter should possess >99.999% microbial removal efficiency. Preferably, the air filter should possess high adsorption capacity for odour and volatile organic compounds.

The air filter in accordance with the present invention is effective against a broad range of bacteria. For example, the air filter is effective in killing *E. carotovora.*

Typical volatile organic compounds (VOC) which may be removed by the adsorbent include one or more of hydrocarbon molecules, such as $C_1$-$C_8$ alkanes. For example, the adsorbent material may be capable of adsorbing any one of or any combination of methane, ethane, butane, methanol, ethanol, butanol, chlorinated compounds, cyclic compounds such as aromatics, for example, benzene, toluene. Suitable volatile organic compounds which may be adsorbed by the adsorbent include typical organic compounds which are present in atmospheric air or effluent streams. For example, hydrocarbons which may be straight chain hydrocarbons and/or branched chain hydrocarbons and optionally substituted with a hydroxyl group or groups, e.g. alcohols, and/or optionally substituted with an aldehyde group or groups.

Suitable volatile organic compounds which may be adsorbed by the adsorbent include those compounds which have a measurable concentration in air by virtue of their vapour pressure under the conditions of the chosen application. Typical volatile organic compounds which may be removed by the adsorbent include one or more of hydrocarbon molecules that are aliphatic, naphthenic or aromatic in nature. For example, the adsorbent material may be capable of adsorbing butane, cyclohexane and toluene.

A VOC may be considered to be any organic compound that has a measurable concentration in air by virtue of its vapour pressure under the conditions in the chosen application. Within European legislation, VOCs have formally been defined to be organic compounds having vapour pressures of 0.01 kPa or more at 20° C. and/or having boiling points of 250° C. or less at atmospheric pressure.

The air filter in accordance with the present invention may comprise a housing structure. Air filter housing structures are well known and typically comprise a means of attachment to the active part or element of the air filter, in this case the combination of polymer foam (further comprising metal particles) and adsorbent or adsorbent polymer foam. The housing structure typically comprises an air inlet and an air outlet. In addition, the housing structure may comprise an air distributer such as an air distributor plate so that the air at the air inlet is more evenly spread when it enters the air filter and thus makes more efficient use of the active part of the air filter.

The air filter in accordance with the present invention provides a number of advantages. The filter kills bacteria rather than simply trapping bacteria and may be easily regenerated. The air filter is also capable of adsorbing volatile organic compounds and therefore capable of eradicating or reducing levels of odours, bacteria, viruses and volatile organic compounds which may in themselves be toxic. In addition, the air filter in accordance with the present invention may be regenerated using heated air or inert gas.

Polymer Foam

The polymer foam may comprise a polymer suitable for use in forming polymer foams. For example, the polymer foam may comprise one or more of polyurethane (PU), poly(vinylpyrrolidinone) (PVP), polyimide (PI), polymers of intrinsic microporosity (PIMs), polyvinylidene difluoride (PVDF), Polyethersulfone (PES), cellulose or bio-degradable polymers such as polylactic acid (PLA) and poly(lactic-co-glycolic acid) (PLGA).

The polymer foam may be formed from one or more of a range of suitable polymers and/or monomers. For example the polymer foam may be formed from one or more of the following: polyethylene glycol (PEG), poly(phenyl isocyanate)-co-formaldehyde, polyol, polyimide, pyromellitic dianhydride.

The polymer foam may be made by combining one or more of the following: monomer which forms the final polymer and/or polymers, metal particles, pore forming agent(s), catalyst, cross-linker(s), solvent and complexing agent. The complexing agent is typically used to form a stable blend of the metal particles with the polymer forming component. For example, in a copper polyurethane foam the composition may be formed from PEG, a solvent such as N-Methyl-2-pyrrolidone (NMP) or Dimethyl sulfoxide (DMSO) and water, a catalyst (e.g. a tin catalyst, and/or an amine catalyst) and an isocyanate. The isocyanate may be selected from one or more of methylene diphenyl diisocyanate (MDI), polymeric MDI (PMDI), toluene diisocyanate (TDI) or polyaryl polymethylene isocyanate (PAPI).

The blowing agent may comprise or consist of any one of or any combination of nitrogen gas, carbon dioxide gas or an organic gas. A suitable organic gas may be chosen from C1-C6 alkane, wherein the alkane may be unsubstituted or substituted with fluorine and/or chlorine.

Particulate Metal

In the various aspects of the invention, the metal may be present as a metal or a metal compound or a metal alloy or any combination of said metal, metal compound or metal alloy. The metal, metal alloy or metal compound possesses antibacterial properties. The metal, metal alloy or metal compound is preferably selected from one of, or any combination of, copper, zinc, silver, potassium, selenium, titanium, gold, palladium, platinum, a compound of any one of copper, zinc, silver, potassium, selenium, titanium, gold, palladium, platinum, an alloy of any one of copper, silver, zinc, potassium, selenium, titanium, gold, palladium, platinum. For example, the particles of metal may comprise a combination of copper and zinc or may comprise a combination of a copper compound and a zinc compound or a combination of copper alloy and zinc alloy.

Suitable copper compounds include one or any combination of copper sulfate, copper oxide, (e.g. CuO and/or $Cu_2O$), copper diazepine, polymeric copper compounds. More generally, copper ions, for example Cu(II) cations. Other suitable examples include copper nanoparticles (e.g. 1 nm-100 nm, for example 3-10 nm). Suitable zinc compounds include one or any combination of zinc oxide, e.g. ZnO, polymeric zinc compounds. Suitable silver compounds include one or any combination of silver sulfadiazine, AgCl, $AgNO_3$, AgBr, AgI, AgS, $Ag_2CO_3$, silver diazepine, polymeric silver compounds, and more generally Ag(I) cations.

The metal or metal compound or metal alloy may be present in a mixture with other metals and/or metal compounds and/or metal alloys or the metal or metal compound or metal alloy may be present in the absence of other metal and/or metal compounds and/or metal alloys. Suitable metal alloys include any one or any combination of the following: CuMgO, CuCaO, CuAgO, CuNiBe, $CuNi_2Be$, $CuCo_2Be$, CuMgO, CuOZnO, $CuAl_8Fe_3$, Cu—$ZrO_2$, ZnO, CuO, $Cu_2O$, Cu, $CuZn_{28}Sn1As$, $CuCo_2Be$, $CuNi_2Be$, $CuZn_5$, CuZnIO, $CuZn_{10}$, $CuZn_{15}$, $CuZn_{20}$, $CuZn_{30}$, $CuZn_{30}As$, $CuZn_{40}$, $CuZn_{28}Sn$, $CuSn_5$, $CuSn_4$.

The present inventors have advantageously found that a combination of zinc with copper helps to retard and/or prevent the precipitation of copper. The metal or metals may be present in the form of cations, e.g. Ag(I), Cu(I) and/or Cu(II) and/or Zn(II) cations. The metal or metals may be present as nanoparticles (1 nm-100 nm). The metals may be present in the form of ions, e.g. $Zn^{2+}$, $Ag^+$, $Cu^+$ or $Cu^{2+}$.

Preferably, the metal is present as any one of copper, zinc, silver or any combination thereof and the copper, zinc, silver may be independently of each other selected from a metal, a metal compound or a metal alloy. The copper and/or zinc and/or silver may also be combined with a further metal, metal alloy or metal compound.

When the metal particle is selected from copper metal, the copper may be pure or essentially pure. For example, the purity may be 20-40%, 40-70% or 70-99.9 wt %. When the metal particle is selected from zinc metal, the zinc may be pure or essentially pure. For example, the purity may be 20-40%, 40-70% or 70-99.9 wt %. When the metal particle is selected from silver metal, the silver may be pure or essentially pure. For example, the purity may be 10-20%, 40-70% or 70-99.9 wt %.

The metal particles act as an antibacterial agent and kill any one or more of a range of bacteria. The metal particles may act as an antifungal agent and kill one or more of a range of fungi. Bacteria and fungi which may be killed through use of the air filter in accordance with the present invention are one or any combination of organisms including: the fungi *Aspergillus niger, Aspergillus flavus, Rhizopus nigricans, Cladosporium herbarium, Epidermophyton floccosum, Trichophyton mentagrophytes, Histoplasma capsulatum*, and the like; bacteria, such as *Pseudomonas aeruginosa, Escherichia coli, Proteus vulgaris, Staphylococcus aureus, Staphylococcus epidermis, Streptococcus faecalis, Klebsiella, Enterobacter aerogenes, Proteus mirabilis*, other gram-negative bacteria and other gram-positive bacteria, mycobactin and the like: yeasts, such as *Saccharomyces cerevisiae, Candida albicans*, and the like. The metal particles may kill spores of microorganisms, viruses and the like.

The metal particles that impart the antimicrobial activity may comprise copper and/or silver in an amount of at least about 20 wt %, or greater than about 30 wt %, at least about 40 wt %, preferably at least about 50 wt % or at least about 60 wt % as calculated on the total of metal (s) present by weight. The metal particles preferably comprise at least copper, and/or copper alloys. The present inventors have found that surprisingly, copper and/or copper alloys have at least the same or even higher antimicrobial activity than silver or silver alloys not comprising copper.

The particulate metal may have a desired particle size and/or particle size distribution. For example, the particulate metal may possess a d50 of about 10-400 μm, about 10-40 μm, about 40-70 μm, about 70-100 μm, about 100-400 μm. Advantageously, the particulate metal may be dispersed homogeneously in the mixture or compositions described herein and provides a desirable high surface area.

Adsorbent

An adsorbent is generally taken to mean a substance that attracts other materials to its surface. The adsorbent material is capable of adsorbing volatile organic compounds (VOC) and toxic gases. The adsorbent material may be or comprise a zeolite including a high silica zeolite or a metal organic framework (MOF). Examples of suitable zeolites are types A and X, silicalite and ZSM-5 high silica zeolites such as HiSiv 3000, HiSiv 1000, ZSM-5, 13X, 3A, 4A, 5A zeolites, powder carbons, carbon, MOFs. A zeolite is a crystalline aluminosilicate of alkali or alkali earth elements such as sodium, potassium and calcium. A MOF is a compound consisting of metal ions or clusters coordinated to organic ligands to form one, two or three dimensional structures. The metal ions or clusters may consist of or comprise one or any combination of Cr, Mg, Ni, Co, Cu, Zn. Examples of particular MOFs include: MIL 101(Cr), (empirical formula $C_{24}H_{17}O_{16}Cr_3$); MOF 177, (empirical formula $Zn_4O(C_{27}H_{17}O_{15}O_6)_2$); MOF 199, (empirical formula $Cu_3(C_9H_3O_6)_2$), MOF 74, (empirical formula $Zn_2(C_8H_2O_6)$); MOF 74 (Mg, Ni, Co) for which any one of, or any combination of, the stated metals may be present. The organic ligands may optionally be selected from, or formed from, one or any combination of: benzene tribenzoate; dihydroxyterephthalic acid, e.g. 2,5-dihydroxyterephthalic acid; carboxylate, e.g. tricarboxylate; amines.

The adsorbent may be present in combination with the polymer in the form of a polymer adsorbent foam.

The zeolite may be represented by the following general formula I:

$$M_{x/n}[(AlO_2)_x(SiO_2)_y]_z H_2O \qquad \text{formula I}$$

where x and y are integers with y/x equal to or greater than 1, n is the valence of the cation M, and z is the number of water molecules in each unit cell of the zeolite structure. In the formula I, n may be selected from 1 or 2 and z may be selected up to a value of 27, for example 1-27 and including all values between 1 and 27. In formula I, M be any suitable cation, for example Na, K, Li, Mg or Ca.

An example of a suitable zeolite type is faujasite. For example, the zeolite may be selected from the general faujasite formula wherein the zeolite may be in any of the sodium, potassium, calcium or magnesium forms:

$$(Na_2, K_2, Ca, Mg)_{3.5}[Al_7Si_{17}O_{48}] \cdot 32(H_2O)$$

Any of the adsorbents mentioned herein may be incorporated in any aspect or any embodiment of the present invention or any combination thereof. This also includes any combination of any of the adsorbents.

Foam Preparation

Generally, the foam in accordance with the present invention may be made by mixing a monomer, polymer or polymer precursor with a suitable solvent. For example, suitable polymers or polymer precursors include polyol or polyethylene glycol (PEG) or pyromellitic dianhydride (PMDA) and a suitable solvent is N-Methyl-2-pyrrolidone (NMP) or Dimethyl sulfoxide (DMSO). To the solution or at least partial solution of monomer, polymer or polymer precursor may be combined a type of cross linker such as an isocyanate. Examples of suitable isocyanates include methylene diphenyl diisocyanate (MDI), polymeric MDI (PMDI), toluene diisocyanate (TDI) or polyaryl polymethylene isocyanate (PAPI). To this mixture may be further combined water (which assists in the formation of a blowing agent, such as $CO_2$), catalyst (e.g. ethanolamine and/or tin or a compound of tin), pore former and metal particles (which may be referred to more generally herein as active agent). Suitable pore formers are selected from PVP, licowax, starch and carbon. The molecular weight of PVP may be about 10 to 58 kD for use in the various aspects and embodiments of the invention, e.g. 10 kD. Typically, the metal or metal compound or metal alloy is added in an amount of about 20-80 wt %, e.g. greater than about 30 wt % based on the total amount of metal particles, monomer, polymer or polymer precursor and cross-linking type moiety (e.g. isocyanate) which is present. In addition, or instead of adding or combining metal particles, adsorbent may be added or combined.

The above constituents may be mixed and homogenised, for example at a stir rate of about 5000-10,000 rpm, e.g. 5000-7000 rpm at about 20° C. for at least about 30 seconds. This creates the blowing agent (e.g. $CO_2$) which assists in the creation of pores. In the systems described in the present invention, the metal particles typically sit or reside, i.e. are located at the edge of the pore cavity and there are gaps in the perimeter of the cavity where the metal may reside or sit.

Antibacterial and Antiviral Metal (e.g. Copper) Polyimide Foam

By way of example, about 5 g of monomer Pyromellitic Dianhydride (PMDA) is mixed with the desired quantity of NMP (approximately 42 mL). PMDA is dissolved in the NMP by stirring in a warm water bath (40-60° C.) until a clear solution is obtained. About 4 mL of water (generally in the range 2-10 ml) is added. 3 drops of catalyst, e.g. ethanolamine is added to this mixture. A small amount of silicon oil, approximately 1.65 g is added and a desired quantity of pore former incorporated, e.g. from about 2 wt % to about 10 wt %. Suitable pore formers include one or more of e.g. PVP (e.g. 10-58 kD), Licowax, starch, carbon. The mixture is stirred with a homogeniser for about 30 s. Metal (e.g. copper) powder is added to the mix to reach the desired weight percentage from about 20-40 wt %, about 40-60 wt % or about 50-80 wt % or about 60-80 wt %, preferably the desired range is about 50-80 wt % or about 60-80 wt %. The amount of copper powder may be greater than about 30 wt %. About 25 μL of catalyst (e.g. tin catalyst) is added and the mixture stirred with a homogeniser for about 30 s to achieve uniform dispersion of active agents (metal particles) and to create microbubbles in the mixture. This step creates additional surface area and porous membranes around the bubbles. The measured amount of isocyanate to the mixture depends on the quantity of monomer used (e.g. ratio 1:1) and is placed in a mould. The monomer mixture is stirred with the homogeniser for about 30 s and this mixture is added to the isocyanate. The mixture is stirred for a further ~5 s and the foam allowed to rise. The foam is removed from the mould. The solvent can be removed either by vacuum drying or through phase inversion with water for 24 hours. Post-treatment is carried out placing the foam into a heated environment between about 60 to about 80° C.

Antibacterial Copper Polyurethane Foam

By way of example, about 5 g of monomer polyol or polyethylene glycol is mixed with the desired quantity of NMP (approximately 42 mL) and about 3 mL of water (typically 2-5 ml). About 3 drops of catalyst (e.g. ethanolamine) is added to this mixture. A small amount of silicon oil, approximately 1.65 g is added and a desired quantity of pore former e.g. from about 2 wt %-about 10 wt %. Suitable pore formers include one or more of e.g. PVP (e.g. 10-58 kD, preferably 10 kD), Licowax, starch, carbon. Copper powder is added to the mixture to reach the desired weight percentage e.g. from about 20-40 wt %, about 40-60 wt % or about 50-80 wt % or about 60-80 wt %, preferably the desired range is about 50-80 wt % or about 60-80 wt %. The amount of copper powder may be greater than about 30 wt %. About 25 μL of catalyst (e.g. tin catalyst) is added and the mixture stirred with a homogeniser for about 30 s to achieve uniform dispersion of active agents (e.g. metal particles such as copper, copper/zinc, silver) and to create microbubbles in the mixture. The mixture is left to cool and to lower the temperature. The measured amount of isocyanate to the mixture depends on the quantity of monomer used (ratio 1:1) and it is placed in the mould. The monomer mixture is stirred with the homogeniser for about 30 s and this mixture is added to the isocyanate. Further stirring is carried out for about 5 s and the foam allowed to rise. The presence of microbubbles creates porous membranes around the bubbles which allows gas molecules access to the active agents. The foam is removed from the mould. The solvent is removed either by vacuum drying or through phase inversion with water for 24 hours. Post-treatment is carried out by placing the foam in a heated environment between about 60° C. to about 80° C.

Adsorbent Polyimide Foam

By way of example, monomer Pyromellitic Dianhydride (PMDA) is mixed with a suitable quantity of NMP approximately 42 mL (typically the range may be about 30-50 ml).

The PMDA is dissolved in the NMP by stirring in a warm water bath (40-60° C.) until a clear solution is obtained and 4 mL of water (range about 2-10 ml) is added. 3 drops of ethanol amine are added to this mixture followed by a small amount of silicon oil, (approximately 1.65 g) and a desired quantity of pore former from about 2 wt % to about 10 wt % is incorporated. Suitable pore formers may be selected e.g. from PVP (e.g. 10-58 kD, preferably 10 kD), Licowax, starch, carbon. The mixture is stirred with a homogeniser for about 30 s. Adsorbent powder (typically crystal size of about 1-13 µm) is added, e.g. 13X zeolite, HiSiv 1000, HiSiv 3000, ZSM-5, 3A, 5A zeolites, high silica zeolites or metal organic frameworks (MOF), to the mix to reach the desired weight percentage from about 60-70%, about 70-80% or about 80-90 wt %. The preferred range is about 70-80 wt %. About 25 µL of tin catalyst (range 15-35 µL) is added and the mixture stirred with a homogeniser for about 30 s to achieve uniform dispersion of active agents and to create microbubbles in the mixture. This step creates additional surface area and porous membranes around the bubbles. Pore former also allows additional porosity in the foam structures and prevents complete polymer coverage of the active zeolite so that the polymer does not block the channels in the adsorbent (e.g. zeolites), thus preventing the size exclusion separation of gas mixtures. The measured amount of isocyanate to the mixture depends on the quantity of monomer used (ratio 1:1) and is placed in the mould. The monomer mixture is stirred with the homogeniser for about 30 s and this mixture is added to the isocyanate. Further stirring for about 5 s ensures that all the zeolites are uniformly distributed throughout the structure, and allow the foam to rise. The foam is removed from the mould. The solvent can be removed either by vacuum drying or through phase inversion with water for about 24 hours. Post-treatment may be carried out by placing the foam in a heated environment between about 300 to 400° C. and under an inert atmosphere.

Adsorbent and Antimicrobial Polyimide Foam (Composite Foam Zeolite Adsorbent and Copper (or Zn/Cu))

By way of example, monomer Pyromellitic Dianhydride (PMDA) is mixed with the desired quantity of NMP (approximately 42 mL; range 30-50 ml). The PMDA is dissolved in the NMP by stirring in a warm water bath (40-60° C.) until a clear solution is obtained. About 2-10 mL of water is added followed by 3 drops of ethanol amine. A small amount of silicon oil is added, i.e. approximately 1.65 g (1-5 g) and a desired quantity of pore former incorporated, typically from about 2 wt % to about 10 wt %. Suitable pore formers may be selected from e.g. PVP (e.g. 10-58 kD, preferably 10 kD), Licowax, starch, carbon. The mixture is stirred with a homogeniser for about 30 s. Adsorbent powder (crystal size of about 1-13 µm), e.g. 13X, HiSiv 1000, HiSiv 3000, ZSM-5, 3A, 5A, high silica zeolites or metal organic frameworks (MOF) is added to the mix to reach the desired weight percentage, e.g. from about 60-70%, about 70-80% or about 80-90%. The preferred range is about 70-80 wt %. Metal powder (e.g. copper or a mix of zinc and copper powder) is added to the mix to reach the desired weight percentage, typically from about 20-40 wt %, about 40-60 wt % or about 60-80 wt %. The preferred range is about 60-80 wt %. The total amount of adsorbent and metal powder in the foam should typically be no more than about 90 wt % and preferably no greater than about 85 wt % (the balance being PI polymer). 25 µL of tin catalyst is added and the mixture stirred with a homogeniser for about 30 s to achieve uniform dispersion of active agents and to create microbubbles in the mixture. The measured amount of isocyanate to the mixture depends on the quantity of monomer used (ratio 1:1) and is placed in the mould. The monomer mixture is stirred with the homogeniser for about 30 s and this mixture added to the isocyanate. Further stirring for about 5 s achieves uniform distribution of active agents throughout the foam and the foam rises. The foam is removed from the mould. The solvent may be removed either by vacuum drying or through phase inversion with water for 24 hours. Phase inversion allows the solidification of polymer and the diffusion of NMP out of the polymer in order to create porous bubbles. Post-treatment is carried out by placing the foam in a heated environment between about 300 to 400° C. under an inert environment. This allows for the redistribution of the polymer and allows the zeolite to come into contact with the VOCs (or $CO_2$) molecules. Polyimide and other high temperature polymers are suitable for this method of preparation due to their high glass transition temperatures (e.g. about 400-500° C.) and their inert chemical nature.

Figure 1B:
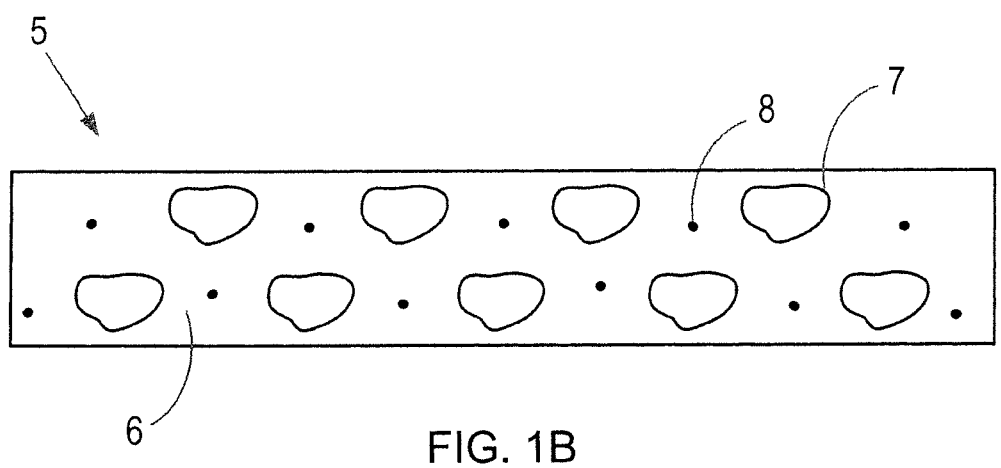
FIG. 1b shows a representation of the combination of polymer foam and adsorbent material suitable for use in an air filter in an embodiment of the invention in the form of a composite.

FIGS. 1a and 1b are representations of the combination of polymer foam, metal particulates and adsorbent material in accordance with the invention. As described herein, these embodiments may be referred to as the active element or active part.

In FIG. 1a, a first substrate of polymer foam (1) comprising particles of metal (2) is illustrated. The metal particles typically possess antimicrobial, e.g. antibacterial properties. The first substrate is deposited on, or in contact with, a second substrate of polymer foam adsorbent or composite (3). In other embodiments, the first substrate may be adjacent to said second substrate. For example, there may be an air gap between said first and second substrates. The air gap may be provided by the use of one or more spacers positioned so as to keep the first and second substrates spaced apart. It will be understood that the first substrate (1) may be deposited on the second substrate of polymer foam adsorbent (3) or the second substrate may be deposited on the first substrate and reference to a first and second substrate may be interchanged, i.e. the first substrate may comprise adsorbent and the second substrate may comprise particles of metal. Pockets of air or gas are also indicated at (4) and (4a). The embodiment in FIG. 1a may be referred to herein as a dual filter. The adsorbent comprised in the second substrate (3) may comprise, consist of, or consist essentially of a zeolite or MOF. In the substrate of polymer foam adsorbent (3), pockets of gas or air are indicated at (4a) and adsorbent material at (25) and are present in the polymer foam (1b).

FIG. 1b represents a composite material (5) suitable for use in an air filter. The composite material (5) comprises a composite of polymer foam, metal particles (8) and an adsorbent, the combination of which are indicated generally at (6). The metal particles typically possess antimicrobial, e.g. antibacterial properties. The adsorbent may comprise, consist of, or consist essentially of a zeolite or MOF. Pockets of air or gas are also indicated at (7). The embodiment in FIG. 1b may be referred to as a composite material.

Figure 2A:
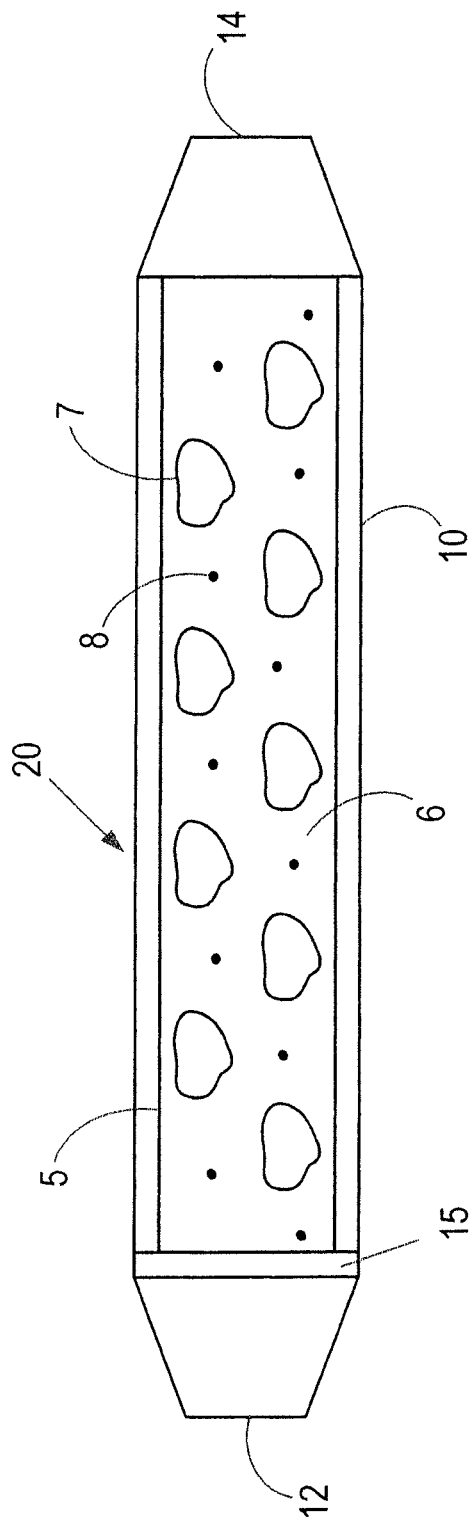
FIGS. 2a and 2b shows an air filter in accordance with the present invention incorporating a polymer foam and adsorbent in the form of a composite and the combination of polymer foam and adsorbent material described in FIGS. 1b and 1a respectively.
Figure 2B:
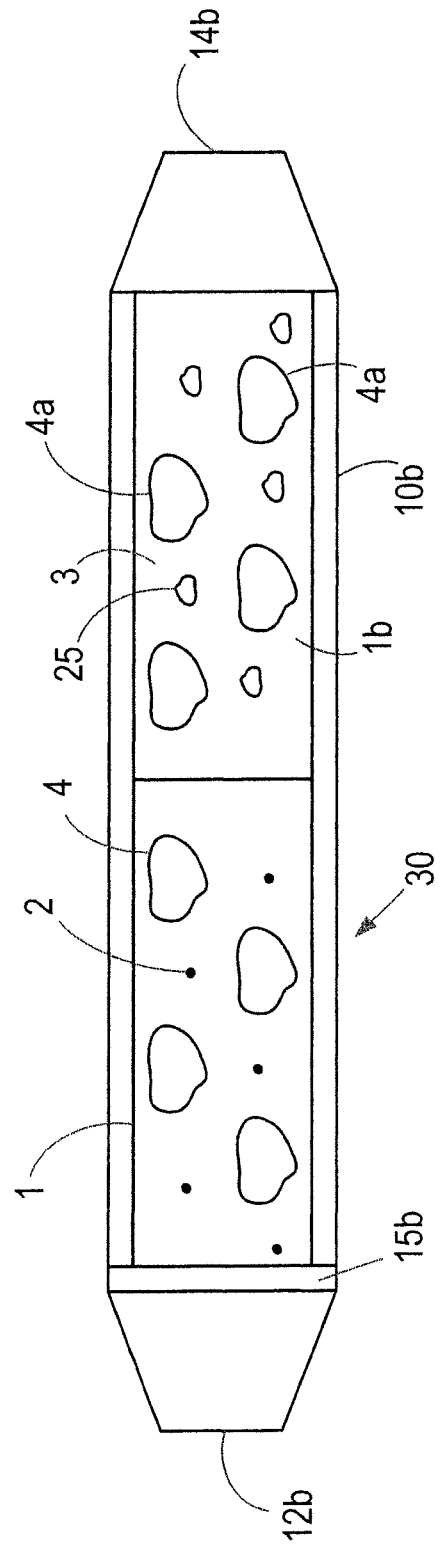

FIGS. 2a and 2b shows the embodiments described in FIGS. 1a and 1b, which may be referred to as active elements, incorporated into an air filter.

In FIG. 2a the composite material (5) is shown located in a filter housing (10). The air filter, indicated generally by (20), comprises an air inlet (12) and optionally an air distributor plate (15). Air enters the air filter at the inlet (12) and if present passes through the air distribution plate (15) so that the air is evenly spread through the composite material (5) as it passes through. After the air passes through the composite material (5) it exits the air filter through the air outlet (14). The air inlet and outlet may be chosen from an appropriate shape, for example it may be circular or square or rectangular in cross section.

In FIG. 2b, the arrangement shown in FIG. 1a is shown incorporated in an air filter. The substrates (1) and (3) are shown in a particular arrangement wherein substrate (1) is shown adjacent the air inlet (12b) and substrate (3) adjacent the air outlet (14b). It will be understood that these substrates may be reversed or multiple arrangements of substrates may be provided. The substrates are shown located in a filter housing (10b). The air filter, indicated generally by (30), comprises an air inlet (12b) and optionally an air distributor plate (15b). Air enters the air filter at the air inlet (12b) and if present passes through the air distribution plate (15b) so that the air is evenly spread through the substrates (1, 3) as it passes through. After the air passes through the substrates (1, 3) it exits the air filter through the air outlet (14b). The air inlet and outlet may be chosen from an appropriate shape, for example they may independently of each other be circular or square or rectangular in cross section.

EXAMPLES

Example 1 describes the loading of 75 wt % copper using polyol (50:50)/PVP/Copper.

Example 2 describes the loading of 33 wt % copper using polyol (50:50) with PVP.

Example 3 describes the preparation of PI/PVP/Copper (75%) foams.

Example 4 describes the preparation of PU (PEG)/copper (55%) anti-bacterial and antiviral foams.

Example 5 describes the preparation of PI/PVP/13X zeolite adsorbent foams.

Example 1 Procedure for PU (Polyol Solution (50% Copper/Zinc, 50% Polyol), Isocyanate)/PVP/Copper Foams (Resulting in 75 wt % Copper)

In Example 1, the following steps were taken.
1. Measure 10 g of Polyol solution (5 g Copper/Zinc, 5 g Polyol) in a 100-ml beaker
2. Measure 42 ml of NMP using a 100-ml beaker and a 10-ml measuring cylinder and add to the Polyol solution
3. Add 3 ml of water using a (100-1000 µl) micro-pipette to the Polyol/NMP solution
4. Add 3 drops of the amine catalyst (ethanol amine) using the plastic pipette
5. Add 1.65 g of silicon oil using a plastic pipette
6. Add 5 wt % (0.5 g—based on the weight of the Polyol polymer/Isocyanate (10 g total)) of PVP (10 kD)
7. Stir the mixture using the homogeniser (IKA® ULTRA-TURRAX® T25 basic) at 6500 rpm for 30 seconds
8. Add 25 g of copper to the solution prepared in Step 7
9. Add 25 µl of the Tin catalyst (dibutyltin dilaurate) using a (10-100 µl) micro-pipette
10. Stir the mixture at 6500 rpm for 30 seconds using the homogeniser
11. Measure 5 g of Isocyanate (poly(phenyl isocyanate)-co-formaldehyde) while waiting for the mixture to cool down to room temperature
12. Stir the mixture again at 6500 rpm for 30 seconds
13. Add the solution prepared in Step 12 to the Isocyanate
14. Stir the solution at 6500 rpm for 5 seconds and allow the foam to rise till the surface feels firm
15. Remove the foam from the glass cylinder slowly and leave it in a water bath for 24 hours to remove the PVP (if was added) and NMP
16. Dry the foam using a paper towel and record the weight of the foam
17. Place the foam on the work bench to dry it further till there is no change in the weight of the foam Example 2 Procedure for PU (Polyol Solution (50% Copper/Zinc, 50% Polyol), Isocyanate)/PVP Resulting in 33% Copper In Example 2, the following steps were taken.
1. Measure 17.2 g of Polyol solution (8.6 g Copper/Zinc, 8.6 g Polyol) in a 100-ml beaker
2. Measure 42 ml of NMP using a 100-ml beaker and a 10-ml measuring cylinder and add to the Polyol solution
3. Add 5 ml of water using a (100-1000 µl) micro-pipette to the Polyol/NMP solution (Adjusted based on the Isocyanate content)
4. Add 3 drops of the amine catalyst (ethanol amine) using the plastic pipette
5. Add 1.65 g of silicon oil using a plastic pipette
6. Add 5 wt % (0.86 g—based on the weight of the Polyol polymer/Isocyanate (17.2 g total)) of PVP (10 kD)
7. Add 25 µl of the Tin catalyst (dibutyltin dilaurate) using a (10-100 µl) micro-pipette
8. Stir the mixture at 6500 rpm for 30 seconds using the homogeniser (IKA® ULTRA-TURRAX® T25 basic)
9. Measure 8.6 g of Isocyanate (poly(phenyl isocyanate)-co-formaldehyde) while waiting for the mixture to cool down to room temperature
10. Stir the mixture again at 6500 rpm for 30 seconds
11. Add the solution prepared in Step 10 to the Isocyanate
12. Stir the solution at 6500 rpm for 5 seconds and allow the foam to rise till the surface feels firm
13. Remove the foam from the glass cylinder slowly and leave it in a water bath for 24 hours to remove the PVP (if was added) and the NMP
14. Dry the foam using a paper towel and record the weight of the foam
15. Place the foam on the work bench to dry it further till there is no change in the weight of the foam Example 3 Procedure for PI (PMDA, Isocyanate)/PVP/Copper Foams (75% Copper)

In Example 3, the following steps were taken.
1. Measure 5 g of PMDA in a 100-ml beaker
2. Measure 42 ml of NMP using a 100-ml beaker and a 10-ml measuring cylinder and add to the PMDA
3. Stir the PMDA/NMP solution under running hot water from the tap until a clear yellow-green solution is obtained
4. Add 4 ml of water using a (100-1000 µl) micro-pipette to the PMDA/NMP Solution
5. Add 3 drops of the amine catalyst (ethanol amine) using the plastic pipette
6. Add 1.65 g of silicon oil using a plastic pipette
7. Add 5 wt % (0.5 g—based on the weight of the PMDA/Isocyanate (10 g total)) of PVP 8. Stir the mixture using the homogeniser (IKA® ULTRA-TURRAX® T25 basic) at 6500 rpm for 30 seconds
9. Add 30 g of copper to the solution prepared in Step 8

10. Add 25 μl of the Tin catalyst (dibutyltin dilaurate) using a (10-100 μl) micro-pipette
11. Stir the mixture at 6500 rpm for 30 seconds using the homogeniser
12. Transfer to long glass tube to allow for homogenous mixing when using the Homogeniser
13. Measure 5 g of Isocyanate (poly(phenyl isocyanate)-co-formaldehyde) while waiting for the mixture to cool down to room Temperature
14. Stir the mixture in the long glass tube at 6500 rpm for 30 seconds.
15. Add the solution prepared in Step 14 to the Isocyanate
16. Stir the solution at 6500 rpm for 5 seconds and allow the foam to rise till the surface feels firm
17 Remove the foam from the glass cylinder slowly and leave it in a water bath for hours to remove the PVP (if was added) and NMP
18. Dry the foam using a paper towel and record the weight of the foam
19. Place the foam on the work bench to dry it further till there is no change in the weight of the foam Foams comprising at least 75 wt % copper may be prepared and typically using about 25 μl of Tin catalyst to provide foams with minimal or no gaps.

Example 4 Procedure for PU (PEG, Isocyanate)/Copper Foams (55% Copper)

In Example 4, the following steps were taken.
1. Measure 5 g of PEG in a 100-ml beaker
2. Measure 15 ml of NMP using a 100-ml beaker and a 10-ml measuring cylinder and add to the PEG
3. Add 0.5 ml of water using a (100-1000 μl) micro-pipette to the PEG/NMP Solution
4. Add 3 drops of the amine catalyst (ethanol amine) using the plastic pipette
5. Stir the mixture using the homogeniser at 6500 rpm for 30 seconds
6. Add 12.2 g of copper to the solution prepared in Step 5
7. Add 25 μl of the Tin catalyst (dibutyltin dilaurate) using a (10-100 μl) micro-pipette
8. Stir the mixture at 6500 rpm for 30 seconds using the homogeniser (IKA® ULTRA-TURRAX® T25 basic)
9. Measure 5 g of Isocyanate (poly(phenyl isocyanate)-co-formaldehyde) while waiting for the mixture to cool down to room temperature
10. Stir the mixture again at 6500 rpm for 30 seconds
11. Add the solution prepared in Step 10 to the Isocyanate
12. Stir the solution at 6500 rpm for 5 seconds and allow the foam to rise till the surface feels firm
13. Remove the foam from the glass cylinder slowly and leave it in a water bath for 24 hours to remove the NMP
14. Dry the foam using a paper towel and record the weight of the foam
15. Place the foam on the work bench to dry it further till there is no change in the weight of the foam Example 5 Procedure for PI (PMDA, Isocyanate)/PVP/13X Zeolite Adsorbent Foams (80 wt % 13X)

In Example 5, the following steps were taken.
1. Measure 5 g of PMDA in a 100-ml beaker
2. Measure 42 ml of NMP using a 100-ml beaker and a 5-ml measuring cylinder and add to the PMDA
3. Stir the PMDA/NMP solution in a warm water bath until a clear yellow-green solution is obtained
4. Add 12.5 ml of water using a (100-1000 μl) micro-pipette to the PMDA/NMP solution as 12 ml of water is required for the zeolites (water capacity—30 wt % based on dry weight) due to the lack of moisture in the zeolite and 0.5 ml of water is required for the foaming reaction.
5. Add 3 drops of the amine catalyst (ethanol amine)
6. Add 1.65 g of silicon oil
7. Add 5 wt % (0.5 g—based on the weight of the PMDA/Isocyanate (10 g total)) of PVP (selected from a range of 10000 to 58000 molecular weights)
8. Stir the mixture using the homogeniser (IKA® ULTRA-TURRAX® T25 basic) at 6500 rpm for 30 seconds
9. Measure 40 g of 13X zeolites and add the solution prepared in Step 8 to the zeolite
10. Stir the mixture using a spatula and cool the solution down in a cold water bath. If required, adjust the viscosity of the solution with NMP.
11. Add 25 μl of the Tin catalyst (dibutyltin dilaurate)
12. Stir the mixture at 6500 rpm for 30 seconds using the homogeniser
13. Measure 5 g of Isocyanate (poly(phenyl isocyanate)-co-formaldehyde) while waiting for the mixture to cool down to room temperature
14. Stir the mixture again at 6500 rpm for 30 seconds and add it to the isocyanate
15. Stir the solution at 6500 rpm for 5 seconds and allow the formation of the adsorbent
16. Post-treatment is carried out by phase inversion in a water bath Pressure Drop Measurements on Examples 1, 2, 3 and 4

Figure 3:
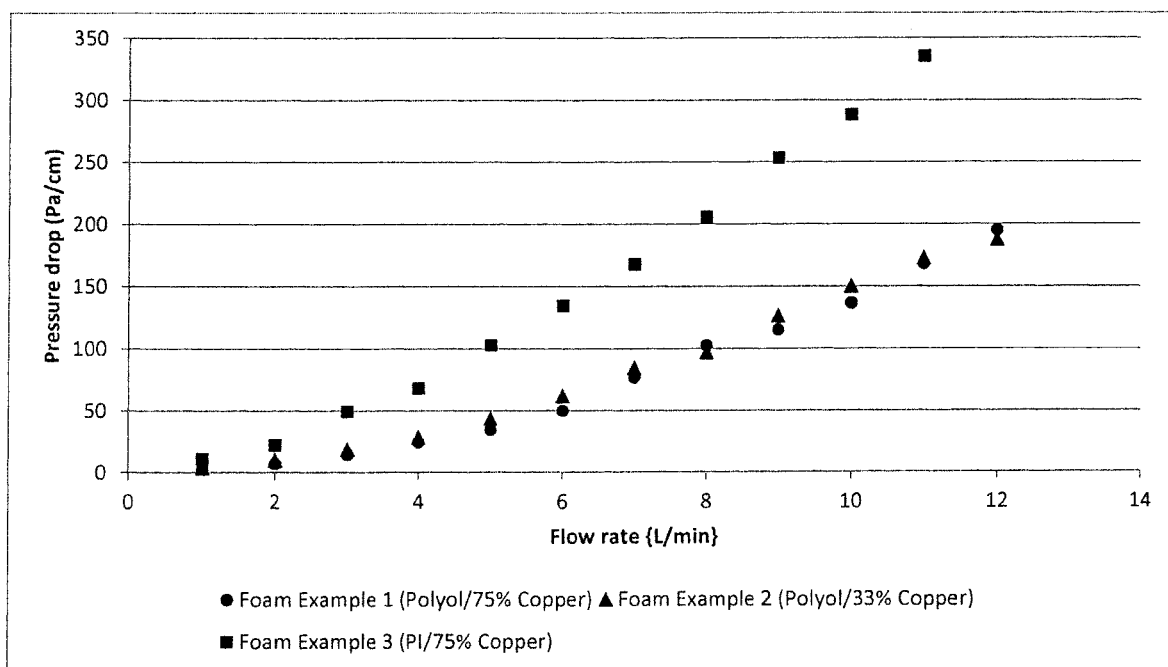
FIG. 3 illustrates the pressure drop on foams in accordance with Examples 1, 2 and 3.

A foam was produced in accordance with Example 4 comprising 55% pure copper (particle size <75 μm), poly (ethylene glycol), poly[(phenyl isocyanate)-co-formaldehyde]. The foam produced in Example 4 was 3.5 cm in length and possessed small pores. The pressure drop measured through the 3.5 cm length of foam at 1 L/min air flow was higher (593 Pa/cm) than the foams produced in accordance with Examples 1, 2 and 3, the results of which are illustrated in FIG. 3.

Bacteria Aerosol Filter Tests on Anti-Bacterial Foams Example 1, 2 and 3 (6-8 cm) and Example 4 (3.5 cm)

Aerosol antimicrobial dynamic testing was carried out in connection with Examples 1 to 4 in order to test the filters in cabin air conditions, the microbial solution was turned into an aerosol with a nebuliser. However, the airplane filter would typically be in the plane for one to one and a half years (time between maintenances). As it was not possible to set such a lengthy experiment, 24 hour experiments were conducted under very stringent conditions (very high humidity, very high bacteria count). A solution of bacteria was prepared by growing *E. carotovora* in medium overnight at 25° C. and diluted to obtain a solution absorbance at 600 nm of ~1. The foams were tested in a tubular module with the bacteria aerosol at 1 L/min and fabric circular discs with absolute barrier filter cloth were used to catch the bacteria through the foams at the outlet of the filter. The discs were changed at regular intervals during the experiment: i.e. at 15 min, 30 min, 60 min, 2 hours, 4 hours, 6 hours and 24 hours. The used disc was washed with 2.5 mL of sterile water to collect the bacteria. 100 μL of the wash out was spread on an Agar plate and placed in an incubator at 25° C. for 24 hours to allow bacteria colonies to grow. The colonies were then counted to assess the efficacy of the filter.

To estimate the log reduction of the foam, it was necessary to estimate the count of bacteria flowing through the system. A fabric disc without a filter was placed in the aerosol bacteria stream for 15 minutes. The filter was washed out in 2.5 mL of water and a dilution of 1000 was applied. 100 μL of the diluted wash out was spread on an Agar plate and a count of colonies after 24 hours in an incubator gave a value of 460. The efficacy of the filter was based on a bacteria count of 460,000 in 15 minutes. The log reduction was then determined based on the colony count per 15 minutes and is presented in Table 1.

TABLE 1

| Colony Count/15 mins | Log reduction |
| --- | --- |
| 1-4 | 99.999% |
| 5-45 | 99.99% |
| 46-459 | 99.9% |
| 460-4599 | 99% |

The results of the bacterial tests are provided in Table 2.

TABLE 2

| | Cumulative number of colonies | | | | | |
| --- | --- | --- | --- | --- | --- | --- |
| Time/mins | Example 1 Polyol/75% copper 7 cm long | Log reduction | Example 2 Polyol/33% copper 8 cm long | Log reduction | Example 3 PI/75% copper 6 cm long | |
| 15 | 0 | 100% | 0 | 100% | 0 | 100% |
| 30 | 0 | 100% | 0 | 100% | 0 | 100% |
| 60 | 409 | 99.99% | 0 | 100% | 8 | 99.999% |
| 120 | 0 | 100% | 0 | 100% | 1 | 99.999% |
| 240 | 162 | 99.999% | 0 | 100% | 0 | 100% |
| 360 | 92 | 99.999% | 5 | 99.999% | 0 | 100% |
| 1440 | 90500 | 99.9% | 1000 | 99.999% | 2671 | 99.99% |

Bacterial Aerosol Testing Results (3.5 cm length) on Example 4

The pure copper foam produced was tested in a dynamic gas flow system with bacteria. The foam filter was a very good fit inside the test module, avoiding any bypass.

The first experiment with aerosol bacterial stream on this foam given in Table 3 showed excellent bacterial log reduction up to 24 hours. The high colony count after 24 hours can be explained due to very high humidity levels in the feed on to the filter and the test module. Also, further aerosol bacterial feed could cause bacteria to carry through to the exit.

The regenerated foam was slightly smaller and did not fit so well within the module explaining the higher colony counts and lower log reductions. To overcome such shrinkage, the foams may be pre-treated at higher temperature (PU at 70° C. and PI at 300° C.-350° C. in inert atmosphere for 24-48 hours).

The Cu foam in Example 4 has a significantly smaller pore structure giving rise to a higher pressure drop and thereby increasing the chances of bacteria being trapped and killed.

TABLE 3

| | Cumulative number of colonies | | | |
| --- | --- | --- | --- | --- |
| Time/mins | Cu powder 55% | Log reduction/ % | Cu powder 55% after regeneration | Log reduction/ % |
| 15 | 0 | 100 | 4 | 99.999 |
| 30 | 0 | 100 | 0 | 100 |
| 60 | 0 | 100 | 0 | 100 |
| 120 | 0 | 100 | 67 | 99.99 |
| 240 | 0 | 100 | | NA |
| 1440 | 438 | 99.99 | | NA |

Bacterial Aerosol Testing Results (long filters) on PU (polyol/Isocyanate)/50% Cu/Zn Bacterial aerosol tests showed that a 7 cm (given in Example 5) long pure Abscents filter was not as effective in achieving the desired log reduction as the foams containing copper. The colony count after 30 minutes was 130 and too high to count after 4 hours. When 32% Abscents-20 wt % Cu/Zn composite foam was tested, it showed that the colony count at the beginning of the experiment was as high as ~3000 but decreased rapidly after. This may be due to a bypass of the bacterial flow around the filter. However, when a composite filter was formed from 2 separate foams of Abscents and Cu/Zn, the bacteria was trapped and the filter was able to achieve the desired reduction. The results presented in Table 4 correspond to aerosol bacterial tests performed on PU (polyol, isocyanate)/50% Cu/Zn long filters. They showed high log reduction from 30 min to 4 hours of the test. The high colony count may be due to the high humidity in the feed forcing a bypass of the filter by the bacteria without much contact with the copper.

TABLE 4

| | Cumulative number of colonies | | | |
| --- | --- | --- | --- | --- |
| Time/mins | Cu/Zn 50% 17 cm | Log reduction/ % | Cu/Zn 50% 19.8 cm | Log reduction |
| 15 | 917 | 99 | 86 | 99.9 |
| 30 | 9 | 99.99 | 0 | 100 |
| 60 | 12 | 99.99 | 6 | 99.99 |
| 120 | 1 | 99.999 | 55 | 99.9 |

TABLE 4-continued

| Time/mins | Cumulative number of colonies | | | |
|---|---|---|---|---|
| | Cu/Zn 50% 17 cm | Log reduction/ % | Cu/Zn 50% 19.8 cm | Log reduction |
| 240 | 15 | 99.99 | 0 | 100 |
| 360 | 260 | 99.9 | 200 | 99.9 |
| 1440 | >1000 | <99.9 | 4800 | 98 |

Bacterial Aerosol Testing Results (for Diluted Stream)

High humidity and high bacteria was observed throughout the experimental set-up after 24 hours experiments in the previous tests.

In practice, cabin air circulation system is generally split and mixed with fresh air. Therefore the bacteria and humidity levels present in cabin air are considerably less than the challenges set up in accordance with the present invention.

The filter was challenged with the bacteria aerosol stream diluted with dry compressed air. The flow rates of each stream were fixed at 500 mL/min to maintain an overall flow rate of 1 L/min. The test performed on a PU: copper/zinc 50% wt foam with this diluted aerosol stream showed high bacteria destruction rates with consistently 99.9% log reduction.

To estimate the log reduction of the foam, it was necessary to estimate the count of bacteria flowing through the system. A fabric disc without a filter was placed in the aerosol bacteria stream for 15 minutes.

The filter was washed out in 2.5 mL of water. 100 μL of the wash out was spread on an Agar plate and a count of colonies after 24 hours in an incubator gave a value of 258. Hence, the efficacy of the filter would be based on a bacteria count of 258 in 15 minutes and is presented in Table 5.

TABLE 5

| Time/mins | Cumulative number of colonies | |
|---|---|---|
| | Cu/Zn 50% 18 cm | Log reduction |
| 15 | 1 | 99% |
| 30 | 1 | 99% |
| 60 | 0 | 100% |
| 120 | 0 | 100% |
| 240 | 2 | 99.9% |
| 360 | 2 | 99.9% |
| 1440 | 17 | 99.9% |

Accumulation of Bacteria Along the Filter Length: Filter Observed by Scanning Electron Microscopy (SEM)

A 10 cm long polyol foam consisting of 35% Cu/Zn was tested with aerosol bacteria. After 24 hours, the foam was cut into 4 shorter lengths and SEM pictures of the centre of the foam of each piece were taken. The length of the foam is cut into 4 sections that is represented by a, b, c and d in FIG. 4.

Figure 4:
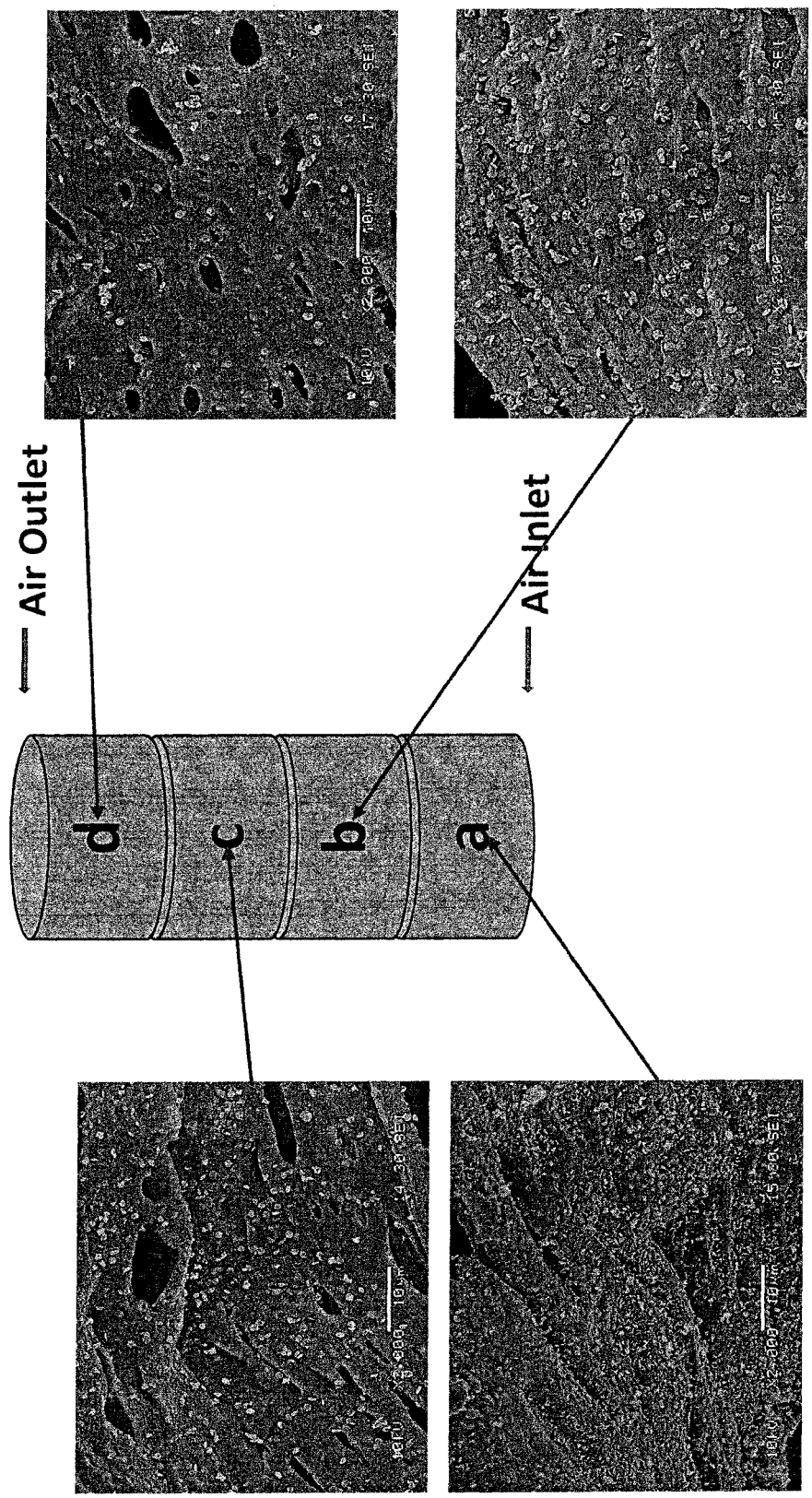
FIG. 4 shows the accumulation of dead bacteria along the length of the filter.

FIG. 4 shows the accumulation of dead bacteria along the length of the filter. The SEM of section a shows the highest accumulation of dead bacteria as the filter gets saturated at the front end. Sections b and c show low dead bacterial counts on the surface of the foam while very few dead bacteria can be observed at the exit (on the top section d) of the filter.

Figure 5:
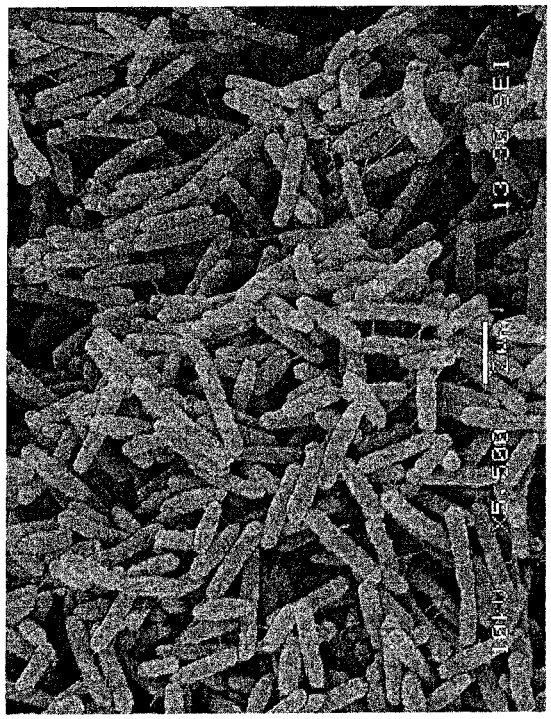
FIG. 5 is SEMs of deformed dead bacteria on 35% Cu/Zn foam compared with the same bacteria when live (*E. carotovora*).
Figure 5:
Figure 6:
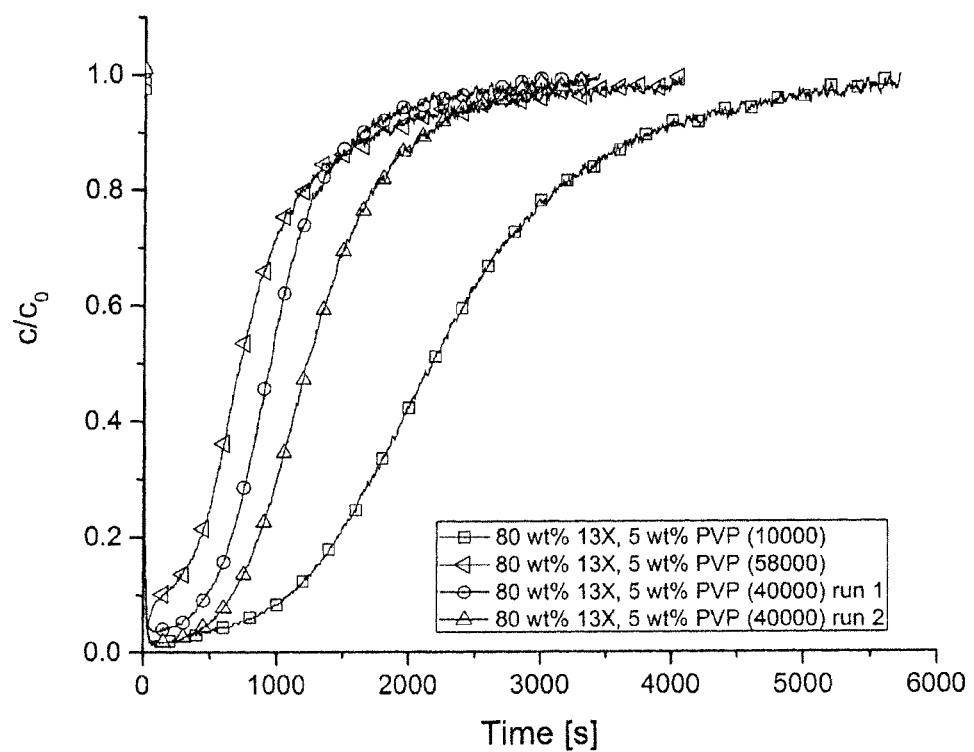
FIG. 6 illustrates $CO_2$ breakthrough testing on foams in accordance with Example 5.

FIG. 5 shows the SEMs of deformed dead bacteria on 35% Cu/Zn foam compared with the same bacteria when live (standard *E. carotovora*).

Dead Live Bacteria Viability Test Carried Out on Example 4

The Live/Dead BacLight assay provided information on the status of the bacterial cell membrane, which is a good indicator of its viability. Staining allowed for the accurate distinction of live and dead bacterial cells as well as monitoring bacterial movement or location. The LIVE/DEAD BacLight assay kit contains two dyes, one called SYTO® 9 and another called propidium iodide. SYTO® 9 passes through the cell membrane of bacteria easily and fluoresces green when a certain wavelength of light shines on it. Propidium iodide, on the other hand, can only enter bacteria with damaged cell membranes. So, once a group of bacteria have been treated with these two dyes, live bacteria appear green and dead bacteria appear red.

To examine the state of the bacteria at the outlet of the filter, fluorescent dyes (red/green) have been used to mark the dead (red) and live (green) bacteria.

The following protocol was used to analyse the bacteria after 24 hours on the absolute barrier filter in connection with Example 4:
  centrifuge 2 mL bacterial suspension;
  wash the pellet 2× with distilled water;
  incubate 15 minutes in fluorescent dye solution (3μl/mL);
  centrifuge the bacteria and wash with diluted NaCl solution;
  dissolve pellet in diluted NaCl solution;
  analyse sample under a microscope using a GFP and RFP filter.

Bacteria viability test was carried out using the wash-out of the absolute barrier filter. The control sample showed the high concentration of green staining, indicating live bacteria. However for Example 4, major proportion of bacteria found to be dead (stained red), confirming the dead bacteria. Only very few appeared green (indicated live).

The dense structure of the copper encapsulated foam, allowed capture of the bacteria and had a sufficient residence time in order to destroy the membrane of the bacteria thus causing death.

More live bacteria were observed after 24 h due to the fact that this copper encapsulated foam had a highly open pore structure allowing an easy path to bacteria to escape without trapping.

Figure 7:
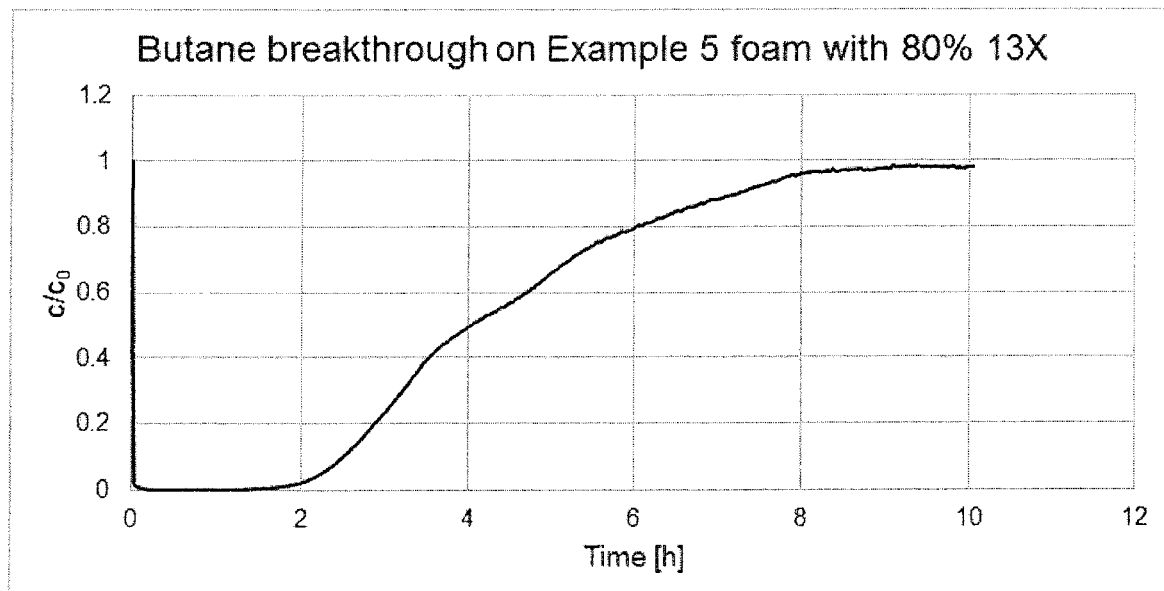
FIG. 7 illustrates adsorption results obtained with 1000 ppm butane challenge on PI/PVP/13X zeolite adsorbent foams (80 wt % 13X, 7 cm length) in connection with Example 5.
Figure 8:
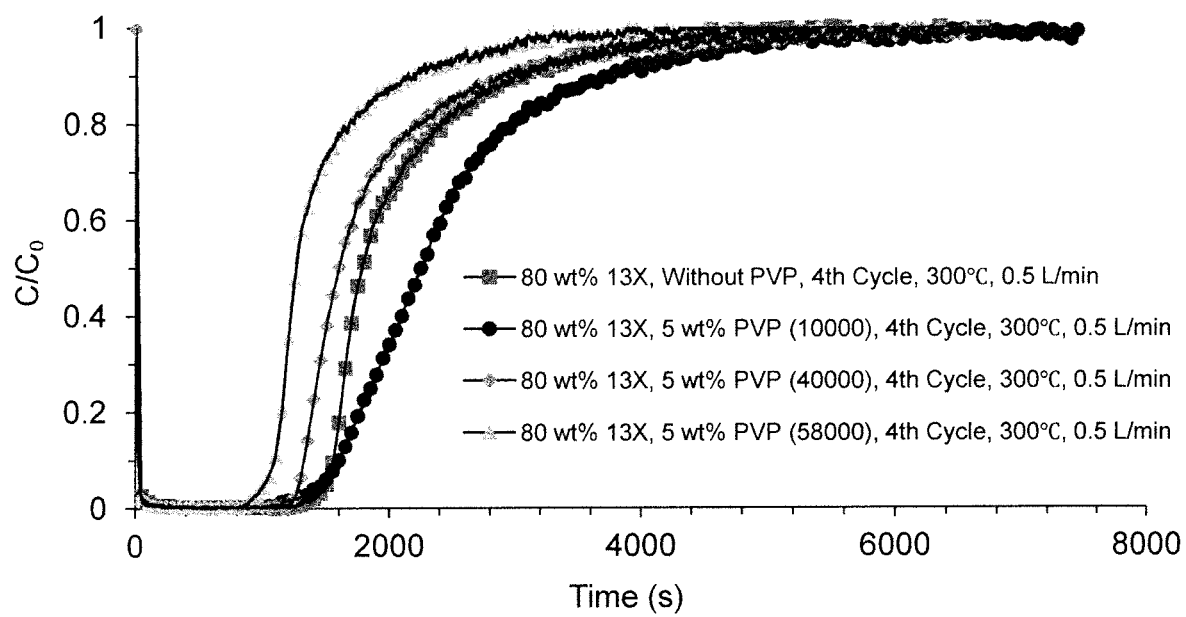
FIG. 8 illustrates adsorption results obtained with 4% $CO_2$ on PI/PVP/13X zeolite adsorbent foams (80 wt % 13X and 5 wt % PVP possessing (i) 10,000 Mwt, (ii) 40,000 Mwt and (iii) 58,000 Mwt) after $4^{th}$ regeneration cycle in connection with Example 5.
Figure 9:
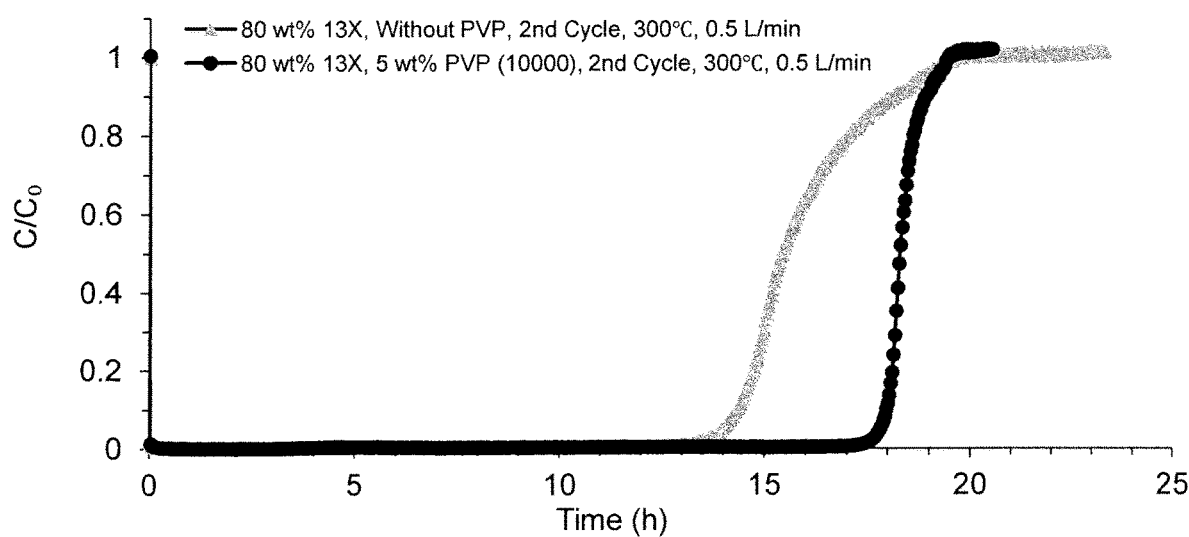
FIG. 9 illustrates adsorption results obtained with 1000 ppm butane challenge on PI/PVP/13X zeolite adsorbent foams (80 wt % 13X), with and without PVP (10,000 Mwt), after $2^{nd}$ regeneration cycle in connection with Example 5.

Testing of Adsorbent Foams in Accordance with Example 5 Using Breakthrough Studies Adsorption breakthrough studies were performed on adsorbent foams of 3.5 cm diameter and 7 cm length fitted in a tubular module. The results presented in FIG. 6 relate to experiments performed with a challenge of 4% vol of $CO_2$ in air at a flow rate of 0.5 L/min and at atmospheric pressure and room temperature. FIG. 8 shows the adsorption results after the $4^{th}$ regeneration cycle. FIG. 7 shows the breakthrough of 1000 ppm of butane at 1 L/min and atmospheric pressure on 80% 13X foam as in Example 5. FIG. 9 shows the adsorption results after the $2^{nd}$ regeneration cycle. The $CO_2$ concentration was measured using an infrared sensor from Edinburgh Sensors Ltd with a range of 0 to 30%. The online hydrocarbon analysis were performed using a Flame Ionisation Detector (FID) from Teledyne. The breakthrough curves obtained were presented in dimensionless concentration ($c/c_0$) vs time and are shown in FIGS. 6, 7, 8 and 9. Before the adsorption experiments, the foams were placed in an oven at 300° C. in an inert atmosphere in order to carry out the post-treatment process.

The invention claimed is:

1. An air filter comprising:
a filter medium formed entirely from a non-fibrous active element, said non-fibrous active element comprising:
a composite of a polymer foam and metal particles; and
an adsorbent material; and
a housing structure containing said filter medium, said housing structure comprising an air inlet and an air outlet,
wherein an entirety of an airflow path from the air inlet to the air outlet is formed by non-fibrous material,
wherein the polymer foam comprises polyimide, and
wherein the metal particles are present in an amount of greater than about 30 wt % to about 80 wt % based on the weight of the polymer foam comprising the polyimide and the metal particles.

2. An air filter according to claim 1, wherein the metal particles are selected from one or any combination of a metal, a metal compound or a metal alloy.

3. The air filter according to claim 1, wherein the filter medium comprises a first layer and a second layer, the first layer comprising the composite of the polymer foam and metal particles and the second layer comprising a composite of the adsorbent material and the composite of the polymer foam and metal particles.

4. The air filter according to claim 3, wherein the first and second layers are in direct physical contact and the first layer is deposited on the second layer.

5. The air filter according to claim 1, wherein said polymer foam, adsorbent material and metal particles are comprised in a composite material.

6. The air filter according to claim 1, wherein the adsorbent material comprises a zeolite and/or carbon and/or a MOF.

7. The air filter according to claim 6, wherein the zeolite is represented by the following general formula I:

$$M_{x/n}[(AlO_2)_x(SiO_2)_y]_z H_2O \quad \text{formula I}$$

where x and y are integers with y/x equal to or greater than 1, n is the valence of the cation M, and z is the number of water molecules in each unit cell of the zeolite structure, and wherein in the formula I, n may be selected from 1 or 2, and z may be selected from 1 to 27.

8. The air filter according to claim 1, wherein the metal particles are selected from one or any combination of copper, zinc, silver, potassium, selenium, titanium, gold, palladium, and platinum, which may be present as metals, metal compounds or metal alloys or any combination thereof.

9. The air filter according to claim 1, wherein the air filter further comprises an air distributor plate.

10. The air filter according to claim 1, wherein the metal particles possess antimicrobial properties.

11. The air filter according to claim 1, wherein the polymer foam further comprises one or more of polyurethane, polymers of intrinsic microporosity (PIMs), polyvinylidene difluoride (PVDF), polyethersulfone (PES), cellulose or bio-degradable polymers.

12. The air filter of claim 5, wherein the metal particles are present in an amount greater than about 50 wt % to about 80 wt % based on the total weight of the polymer foam comprising the polyimide and the metal particles, and wherein the metal particles are selected from one or any combination of copper, zinc, silver, potassium, selenium, titanium, gold, palladium, and platinum, which are present as metals, metal compounds or metal alloys or any combination thereof.

13. The air filter according to claim 12, wherein the metal particles are selected from one or any combination of copper, zinc and silver.

14. A method of making the air filter of claim 1, said method comprising:
providing the housing structure with the air inlet and the air outlet; and
providing the filter medium by forming a mixture the steps of forming the mixture comprising:
(i) dissolving a monomer, polymer precursor or polymer in a solvent to form a solution;
(ii) combining the solution from (i) with water to form a blowing agent; and further combining therewith;
(iii) an isocyanate;
(iv) a catalyst;
(v) a pore former;
(vi) the metal particles; and
(vii) homogenising the mixture.

15. A method according to claim 14, further comprising drying the mixture.

16. A method according to claim 14, wherein in (i) the monomer, polymer precursor or polymer are selected from polyol, PEG, PMDA, PI, PIMs, PVDF, PES and/or in (ii) the blowing agent is $CO_2$ and/or in (iii) the isocyanate is methylene diphenyl diisocyanate (MDI), polymeric MDI (PMDI), toluene diisocyanate (TDI) or polyaryl polymethylene isocyanate (PAPI) and/or in (iv) the catalyst is selected from ethanol amine or a tin catalyst and/or in (v) the pore former is selected from PVP, licowax, starch, carbon and/or in (vi) the metal particles are selected from one or any combination of copper, zinc, silver, potassium, selenium, titanium, gold, palladium, and platinum, in the form of metals, metal compounds or metal alloys or any combination thereof, and/or in (vii) homogenisation takes place at about 20° C. or at least about 20° C., and/or at about 5000 rpm or at least about 5000 rpm.

17. A method of filtering air comprising contacting the air filter of claim 1 with air, wherein the metal particles are selected from one or any combination of copper, zinc, silver, potassium, selenium, titanium, gold, palladium, platinum, which are present as metals, metal compounds or metal alloys or any combination thereof.

18. An air filter according to claim 1, wherein the metal particles are present in an amount of about 50 wt % to about 80 wt % based on the weight of the polymer foam comprising the polyimide and the metal particles.

19. An air filter according to claim 1, wherein the metal particles are present in an amount of about 60 wt % to about 80 wt % based on the weight of the polymer foam comprising the polyimide and the metal particles.

20. The method of claim 14, wherein the blowing agent is further combined with the adsorbent material.

21. The method of claim 20, wherein the adsorbent material is selected from a zeolite and/or carbon and/or an MOF.

22. A method according to claim 20, wherein the adsorbent material comprises a zeolite and/or carbon and/or an MOF.

23. A method according to claim 22, wherein the zeolite is represented by the following general formula I:

$$M_{x/n}[(AlO_2)_x(SiO_2)_y]_zH_2O \qquad \text{formula I}$$

where x and y are integers with y/x equal to or greater than 1, n is the valence of the cation M, and z is the number of water molecules in each unit cell of the zeolite structure, and wherein in the formula I, n may be selected from 1 or 2, and z may be selected from a value of 1 to 27.

* * * * *